United States Patent [19]

Flesher et al.

[11] Patent Number: 5,104,790
[45] Date of Patent: Apr. 14, 1992

[54] MONOCLONAL ANTIBODIES TO SPECIFIC ANTIGENIC REGIONS OF THE HUMAN IMMUNODEFICIENCY VIRUS AND METHODS FOR USE

[75] Inventors: Alan R. Flesher, Seattle; Mary K. Shriver, Bellevue, both of Wash.

[73] Assignee: Genetic Systems Corporation, Redmond, Wash.

[21] Appl. No.: 105,761

[22] Filed: Oct. 7, 1987

Related U.S. Application Data

[63] Continuation-in-part of Ser. No. 67,996, Jun. 29, 1987, abandoned, which is a continuation-in-part of Ser. No. 45,026, May 1, 1987, abandoned, which is a continuation-in-part of Ser. No. 898,273, Aug. 20, 1986, abandoned.

[51] Int. Cl.$^5$ .................................. G01N 33/569
[52] U.S. Cl. ................................ 435/5; 435/240.27; 435/974; 435/975; 530/387.9; 530/388.35
[58] Field of Search ............... 435/5, 240.27, 974, 435/975; 530/387

[56] References Cited

U.S. PATENT DOCUMENTS

| | | | |
|---|---|---|---|
| 4,629,783 | 12/1986 | Cosand | 530/324 |
| 4,753,873 | 6/1988 | Beltz et al. | 435/5 |
| 4,755,457 | 7/1988 | Robert-Guroff et al. | 435/5 |
| 4,843,011 | 6/1989 | Sarngadharan et al. | 435/240.27 |
| 4,888,290 | 12/1989 | Kortright et al. | 435/240.27 |

OTHER PUBLICATIONS

Chassagne et al., "A Monoclonal Antibody Against LAV 'GAG' Precursor: Use For Viral Protein Analysis and Antigenic Expression in Infected Cells" J. Immunol., 136(4) 1442-1445 (1986).
Chang et al., "Expression in Escherichia coli of Open Reading Frame Gene Segments of HTLV-III", Science (1985) 228:93-96.
Steimer et al., "Differential Antibody Responses of Individuals Infected With Aids-Associated Retroviruses Surveyed Using the Viral Core Antigen p. 25 GAG Expressed in Bacteria", Virol. 150 (1986) pp. 283-290.
Robert-Guroff et al., "HTLV-III—Neutralizing Antibodies in Patients With Aids-Related Complex," Nature 316 (1985) 72-4.
Veronese et al., "Monoclonal Antibodies Specific for p. 24, the Major Core Protein of Human-T-Cell Leukemia Virus Type III", Proc. Natl. Acad. Sci. U.S.A., 82(1985) 5199-5202.
Kanner et al., "Human Retroviral env and gag Polypeptides: Serologic Assays to Measure Infection", J. Immunol. 137(1986) 674-678.
Dowbenko et al., "Bacterial Expression of the Acquired Immunodeficiency Syndrome Retrovirus p. 24 gag Protein and Its Use as a Diagnostic Reagent", Proc. Natl. Acad. Sci. U.S.A., 82(1985) 7748-52.

*Primary Examiner*—Christine Nucker
*Attorney, Agent, or Firm*—Townsend and Townsend

[57] ABSTRACT

Monoclonal antibodies capable of binding antigenic determinants within regions of the core proteins of the Human Immunodeficiency Virus and immortalized cell lines producing those monoclonal antibodies are provided. The monoclonal antibodies find use in a variety of ways, including HIV antigen detection in biological samples. Using these methods, individuals may be identified who are infected with HIV but who have not yet developed anti-HIV antibodies. The methods also find use in monitoring in vitro growth of HIV, and the efficacy of therapeutic agents and vaccines.

12 Claims, No Drawings

MONOCLONAL ANTIBODIES TO SPECIFIC ANTIGENIC REGIONS OF THE HUMAN IMMUNODEFICIENCY VIRUS AND METHODS FOR USE

CROSS-REFERENCE TO RELATED APPLICATIONS

This application is a continuation-in-part application of U.S. Ser. No. 067,996, filed June 29, 1987, which is a continuation-in-part application of U.S. Ser. No. 045,026, filed May 1, 1987, which is a continuation-in-part application of U.S. Ser. No. 898,273, filed Aug. 20, 1986, all of which are abandoned and are incorporated herein by reference.

TECHNICAL FIELD

The present invention relates generally to novel immunological materials useful in diagnosing and monitoring infections caused by the Human Immunodeficiency Virus (HIV), the etiologic agent of AIDS. More particularly, the invention provides cell lines which produce monoclonal antibodies to antigenic determinants of the core proteins of HIV. These antibodies are useful in the diagnosis of HIV infection and monitoring the efficacy of pharmaceutical formulations and vaccine compositions.

BACKGROUND OF THE INVENTION

The etiologic agent of Acquired Immune Deficiency Syndrome (AIDS) is a novel lymphotropic retrovirus termed the Human Immunodeficiency Virus (HIV), which may also be referred to in the literature as LAV, HTLV-III, or ARV. As the spread of HIV reaches pandemic proportions, preventing its transmission has become a paramount concern. To reduce the risk of transfusion-associated HIV infection, hospitals, blood banks, and other users or manufacturers of blood-related products now routinely screen blood donors for the presence of antibodies to HIV. The screening tests typically employ disrupted preparations of purified HIV which have been adsorbed onto a solid surface, such as a microwell or bead. Other screening tests use HIV polypeptides produced by recombinant means, or chemically synthesized peptides which contain immunodominant antigenic regions of HIV. Using such screening tests, the vast majority of the potentially infective units of blood in the donor pool are identified and removed.

Despite the high sensitivity and specificity of the HIV antibody screening tests, a small but significant number of infected blood products still pass undetected into the blood supply. Of primary concern are donors who are infected with HIV at the time they donate blood or plasma but have not yet developed antibodies to the virus. Antibodies may not rise to detectable titers until 3–4 weeks or more after infection. Recent evidence puts the window between time of infection and development of detectable antibody at six weeks to six months. If an infected individual donates blood or plasma during this period, the public blood supply is threatened with an undetected contamination.

To help bridge the gap between the time of initial infection and subsequent seroconversion, a sensitive and specific test for HIV antigens is desirable. Using conventional enzyme immunoassay technology, HIV antigen detection tests have been developed in which polyclonal antibodies to HIV are used to "capture" HIV antigen from a patient or culture sample. The polyclonal antibodies take the form of sera which have been obtained from patients having high antibody titers to HIV, or has been generated in amimal species by immunization. These polyclonal based antigen capture tests have been found to correlate well with the appearance of reverse transcriptase (RT) activity in cell cultures, and they are faster and easier to perform than the RT assay. The use of antisera, however, frequenctly imparts a lack of specificity to the tests, which may yield high background readings, require relatively long incubation periods, and may pose a number of difficulties in the manufacturing process.

Monoclonal antibodies of high affinity and specificity to certain conserved epitopes of HIV could provide a significant improvement over the polyclonal based antigen capture assays described above. While several groups have reported monoclonal antibodies which bind to HIV, the suitability of these antibodies for use in antigen capture assays is unknown. What is needed in the art are monoclonal antibodies specific for conserved antigenic regions of HIV proteins, which antigens are present soon after an individual becomes infected with HIV and, desirably, may be detected with the monoclonal antibodies prior to seroconversion. The present invention fulfills these and other related needs.

SUMMARY OF THE INVENTION

Immortalized cell lines which produce monoclonal antibodies have been generated, which antibodies are specific for epitopes of antigenic determinants within a region of the core proteins of HIV defined by a recombinant fusion protein, pGAG3. Of particular interest are monoclonal antibodies which react with antigenic determinants encoded within the DNA sequences from about base pair (bp) 1167 through about bp 1292, from about bp 1278 through about bp 1385, and within the latter sequence, from about bp 1320 through 1385. These regions correspond to the amino acid sequences of peptides 147, 88, and 15, respectively. Also provided are monoclonal antibvodies which bind to antigenic determinants encoded within the DNA sequences of pGAG1, pGAG2, and pGAG3. More particularly, the antibodies bind to antigenic determinants encoded within bp 691 to about bp 961, from bp 927 through about bp 1061 (peptide 141), or from about bp 927 through about 961.

The monclonal antibodies of the invention provide a method for detecting and/or quantitating HIV in a biological sample suspected of containing the virus or antigenic determinants thereof. The antigen detection method comprises incubating the sample with one or more capture monoclonal antibodies, wherein the antibodies are specific for an HIV antigenic determinant within the gag regions enumerated above. The sample and capture antibodies may be incubated simultaneously or sequentially with a second antibody composition which may be labeled or unlabeled, thereby forming a reaction mixture. If the second antibody composition is labeled, the reaction mixture is then detected to determine the amount of label associated with HIV. If the second antibody composition is unlabeled, a third labeled composition is necessary to provide for detection. The second antibody composition may be selected from the group consisting of antibodies which bind to the capture antibodies, monoclonal antibodies of the present invention, monoclonal antibodies to other determinants of HIV, and polyclonal antiserum, the latter being obtained from humans previously exposed to HIV and containing antibodies to the virus, or animals immunized with antigenic portions of the virus.

DESCRIPTION OF THE SPECIFIC EMBODIMENTS

In accordance with the present invention, novel monoclonal antibodies that bind to antigenic determinants contained within certain regions of the core (or gag) proteins of HIV are provided. The monoclonal antibodies bind to proteins and protein precursors of HIV clinical isolates which contain the targeted regions of antigenic determinants, in addition to binding to recombinant proteins and synthetic analogues of the proteins which contain the antigenic determinants. The immortalized cells which produce the monoclonal antibodies have identifiable chromosomes which encode an antibody or fragment thereof having a binding site for an epitope of an antigenic determinant contained within the gag protein regions described more fully below, which antigenic determinant is conserved among HIV clinical isolates. The monoclonal antibodies produced by the immortalized cells find use separately or in combination in a wide variety of ways, including diagnostic immunoassay methods.

The preparation of monoclonal antibodies can be accomplished by immortalizing the expression of nucleic acid sequences that code for antibodies or binding fragments therefor specific for HIV, by introducing such sequences into a host capable of cultivation in culture. The immortalized cell line may be a mammalian cell line that has been transformed through oncogenesis, by transfection, mutation or the like. Such cells include myeloma lines, lymphoma lines, or other cell lines capable of supporting the expression and secretion of the antibody in vitro. The antibody may be a naturally occurring immunoglobulin of a mammal, produced by transformation of a lymphocyte, particularly a splenocyte, by means of a virus of by fusion of the lymphocyte with a neoplastic cell, e.g., a myeloma, to produce a hybrid cell line. Typically, the splenocyte will be obtained from an animal immunized against the HIV virus or a fragment thereof containing an antigenic determinant within a region of the gag proteins recognized by the monoclonal antibodies of the present invention.

Immunization protocols are well known and can vary considerably yet remain effective (See, Goding, 1983, *Monoclonal Antibodies: Principles and Practice*, Academic Press, N.Y,., incorporated herein by reference, and commonly owned pending U.S. patent applications Ser. Nos. 898,273, 045,026, and 067,996). Immunogenic amounts of antigenic preparations are injected, generally at concentrations in the range of 1 ug to 20 mg/kg of host. Administration of the antigenic preparations may be one or a plurality of times, usually at one to four week intervals. Immunized animals are monitored for production of antibody to the desired antigenic determinants or gag proteins containing the desired determinants, the lymphoblastoid cells are then removed and B lymphocytes isolated and transformed of fused with a myeloma cell line. The fusion or transformation can be carried out in conventional ways, the fusion technique being described in an extensive number of patents. See generally, U.S. Pat. Nos. 4,172,124; 4,350,683; 4,363,799; 4,381,292; and 4,423,147. See also, Kennett et al., 1980, *Monoclonal Antibodies*, Plenum, New York, and references cited therein, and Goding, supra, all of which are incorporated herein by reference.

The immortalized cell lines may be cloned and screened by modification of conventional techniques, and antibodies in the cell supernatants detected which are capable of binding to the desired regions of antigenic determinants of HIV, as determined by binding to recombinant fusion proteins or synthetic peptides which contain the region of the antigenic determinants of interest. The appropriate immortalized cell lines may then be grown in large scale culture in vitro or injected into the peritoneal cavity of an appropriate host for production of ascites fluid. By virtue of having the antibodies of the present invention, other cell line supernatants may be screeen in competition with the subject monoclonal antibodies in a competitive assay. Thus, immortalized cell lines can be readily produced from a variety of sources based on the availability of the present monoclonal antibodies. Cell lines that produce monoclonal antibodies which are capable of reacting with the HIV antigenic regions identified herein, as well as those which block the binding of antibodies described below in a competitive assay, are specifically included within the scope of the present invention.

Alternatively, the immortalized cell lines of the present invention may be fused with other neoplastic B-cells, where such other B-cells may serve as recipients for genomic DNA coding for the antibody. Or, using recombinant DNA techniques, the monoclonal antibody or fragment thereof may be produced by inserting genomic DNA or cDNA coding for one or both heavy and light chains into an expression vector for ultimate expression of the chains. These chimeric antibodies may be constructed wherein the antigen binding fragment of an immunoglobulin molecule (variable region) is connected by a peptide linkage to at least part of another protein, such as the constant portion of a human immunoglobulin molecule. This can be accomplished by fusing the variable region genes with constant region genes of the desired species source and subtype. See, for example, European patent publications Nos. 171,496 and 173,494.

While rodent, particularly murine, neoplastic B-cells are preferred, other mammalian species may be employed, such as human, lagomorpham, bovine, ovine, equine, porcine, avian or the like, so long as the species recognizes the regions of the gag protein containing the determinants as antigenic and can provide lymphocytes, particularly splenocytes, for fusion or transformation.

The monoclonal antibody secreted by the transformed or hybrid cell lines may be of any of the classes or subclasses of immunoglobulins, such as IgM, IgD, IgA, or subclasses of IgG known for each species of animal. As IgG is the most common isotype utilized in diagnostic assays, it is preferred for this purpose. The monoclonal antibodies may be used intact, or as fragments, such as Fv, Fab, F(ab')$_2$, but usually intact.

Monoclonal antibodies of the present invention are particularly useful in diagnostic assays because of their specificity for HIV antigenic determinants of the gag proteins, which determinants are within protein regions defined by immunologically reactive recombinant fusion proteins and peptide sequences. Using a variety of recombinant fusion proteins and synthetically constructed HIV peptides (see commonly owned U.S. Pat. No. 4,629,783, and U.S. Ser. No. 763,460, 828,828 and 844,485, which are incorporated herein by reference) the monoclonal antibodies of the present invention may be identified as binding to antigenic determinants within regions encoded by gag sequences of the HIV genome.

The recombinant fusion proteins and synthetic peptides which define the antigenic regions of interest are all encoded within the gag region of the HIV genome. Of particular interest are regions within the gag open reading frame defined by the recombinant fusion protein GAG3, which is encoded by a DNA sequence pGAG3, which extends from about base pair (bp) 691 to about 1642 fo the LAB$_{BRU}$ isolate of HIV. Within the region encoded by pGAG3, antigenic determinants encoded by nucleotide sequences included within and encoded by pGAG1 and pGAG2 are also of interest. The area of overlap between pGAG1 and pGAG3 extends from about bp 691 to about 961, and the area of overlap between pGAG2 and pGAG3 extends from about bp 691 to about bp 1224. The numbering is according to Wain-Hobson et al., 1985, *Cell* 44:9, which is incorporated herein by reference. The production of the recombinant gag fusion protein is described in detail in commonly owned U.S. patent applications U.S. Ser. No. 763,460 and 828,828, both of which are incorporated herein by reference. Of further interest are monoclonal antibodies which bind to antigenic determinants encoded within the DNA sequence from about bp 691 to about bp 1061, including the region encoded by from about bp 927 through about bp 1061. Also of interest are antibodies which bind to the antigenic determinants encoded by the DNA sequence of HIV from about bp 1167 through about bp 1385, particularly the determinants encoded within the regions of about bp 1167 through about bp 1292, and bp 1278 through about bp 1385.

Synthetic peptides within the p25 core protein regions containing the antigenic determinants to which the monoclonal antibodies of present invention bind have been synthesized. These include peptide I, also designated 141, which extends from about amino acid residue 198 to about 242 (bp 927 to 1061) and has the following amino acid sequence, where oligopeptides within the following sequence will include linear epitopes within such sequence:

(Cys—Gly—Gly—Cys)—Met—Gln—Met—Leu—Lys— I (141)
—Glu—Thr—Ile—Asn—Glu—Glu—Ala—Ala—-
Glu—Trp—
—Asp—Arg—Val—His—Pro—Val—His—Ala—Gly—-
Pro—
—Ile—Ala—Pro—Gly—Gln—Met—Arg—Glu—-
Pro—Arg—
—Gly—Ser—Asp—Ile—Ala—Gly—Thr—Thr—Ser—-
Thr—(Cys)

where the amino acids within the parentheses have been added for ease of synthesis or possible post synthetic uses known to those skilled in the art.

Peptide II, also designated 147, of the p25 region of the gag open reading frame is comprised of the amino acid residues encoded from about bp 1167 to about bp 1292 and has the following amino acid sequence, where oligopeptides included within the following sequence will include linear epitopes within such sequence:

(Cys—Gly—Gly—Cys)—Ser—Pro—Thr—Ser—Ile— II (147)
—Leu—Asp—Ile—Arg—Gln—Gly—Pro—Lys—Glu—-
Pro—
—Phe—Arg—Asp—Tyr—Val—Asp—Arg—-
Phe—Tyr—Lys—
—Thr—Leu—Arg—Ala—Glu—Gln—Ala—Ser—Gln—-
Glu—

-continued

—Val—Lys—Asn—Trp—Norleu—Thr—Glu—(Gly—-
Cys)

where the amino acids within the parenthesis have been added for ease of synthesis or possible post synthetic use. Peptide III, also designated 88, comprises an antigenic determinant from the p25 region of the gag open reading frame and contains the amino acid residues encoded from about bp 1278 to about bp 1385 and is made up of the following amino acid sequence, and is further described in pending U.S. Patent application Ser. No. 844,485, included herein by reference:

($NH_2$—Cys)—Asn—Trp—Norleu—Thr—Glu—Thr— III (88)
—Leu—Leu—Val—Gln—Asn—Ala—Asn—Pro—As-
p—Cys—
—Lys—Thr—Ile—Leu—Lys—Ala—Leu—Glu—-
Pro—Ala—Ala—
—Thr—Leu—Glu—Glu—Norleu—Norleu—-
Thr—Ala—Cys Wherein the amino acids within the parenthesis have been aded for ease of synthesis or possible post synthetic use. Alternatively, truncated sequences of peptide III have been prepared. In this regard, the following sequence may be particularly useful and is further described in issued U.S. Pat. No. 4,629,783:

($NH_2$—Cys—Gly)—Asp—Cys—Lys—Thr—Ile— IV (15)
—Leu—Lys—Ala—Leu—Gly—Pro—Ala—Ala—-
Thr—Leu—
—Glu—Glu—Norleu—Norleu—Leu—Thr—Ala—Cys For diagnostic uses, methods such as the enzyme linked immunoadsorbent assay (ELISA), radioimmunoprecipitation assay, and immunoblotting are typically employed. Generally these procedures are well known in the art. See, *Immunological Methods*, Vols. I and II, 1979 and 1981, Eds, Lefkovits and Pernis, Academic Press, New York; *Monoclonal Antibodies*, 1982, eds. Kennett, et al., Plenum Press, New York; and *Handbook of Experimental Immunology*, 1978, ed. Weir, Blackwell Scientific Publications, St. Louis, Mo; all of which are incorporated herein by reference.

Typically, the diagnostic immunoassays will entail the detection of immune complexes formed between the capture monoclonal antibody and the HIV antigen possessing an epitope on an antigenic determinant from a region defined by the above preferred sequences. Generally, to provide for detection the antibodies may either be labeled or unlabeled. A wide variety of labels may be employed, such as radionuclides, fluorescers, enzymes, enzyme substrates, enzyme cofactors, enzyme inhibitors, ligands (particularly haptens), etc. Numerous types of immunoassays are available, and by way of example, some include those described in U.S. Pat. Nos. 3,817,827; 3,850,752; 3,901,654; 3,935,074; 3,984,533; 3,996,345; 4,034,074; 4,098,876; and 4,376,110, all of which are incorporated herein by reference. When unlabeled, detection can be accomplished in agglutination assays. In addition, unlabeled antibody compositions can be used in combination with other labeled, antibodies (second antibodies) that are reactive with the antibody compositions, such as antibodies specific for immunoglobulin.

In general it is necessary to at least partially purify the monoclonal antibody from the ascites fluid or culture supernatants before labeling. Methods of purification are well known (Mishell, et al., supra), and can include ammonium sulfate fractionation, ion exchange chromatography, gel filtration chromatography, affinity chromatography, or some combination thereof.

The monoclonal antibodies of the present invention find particular use in sandwich enzyme immunoassays to capture and detect HIV or antigenic portions thereof. A biological sample suspected of containing HIV antigens is combined with the subject monoclonal antibodies, which may be first attached to a solid support. The sample is then reacted with the monoclonal antibody or antibodies under conditions conducive to immune complex formation and binding occurs between the antibodies and those molecules exhibiting the selected antigenic determinants of HIV. The immune complexes may then be separated from uncomplexed material then and, if the capture antibody is labeled, signal is detected. If the capture antibody is unlabeled, a second antibody, which may be a monoclonal antibody of the present invention, polyclonal antisera to HIV, or an antibody to the capture antibody, and may be labeled or unlabeled, is added. If the second antibody composition is labeled the presence of the antibody-label conjugate specifically bound to the antigen is determined. In a convenient embodiment, the second antibody composition is labeled, and is incubated simultaneously with the sample and capture antibodies. If the second antibody composition is unlabeled, a third antibody composition conjugated to a label may be used. Other conventional techniques well known to those skilled in the art may also be utilized. For instance, in another embodiment, a method for determining the presence of HIV in a biological sample comprises incubating a monoclonal antibody of the present invention with a biological sample, and detecting the presence of immune complexes formed between the monoclonal antibody and the antigenic determinant of HIV, and therefrom determining the presence or absence of HIV.

The biological sample tested for the presence of HIV may comprise a physiological fluid, such as human serum, saliva, semen, vaginal secretions, or breast milk, human tissues, cerebrospinal fluid, or cell culture supernatants or the like.

The capture antibodies may be affixed to a solid support in a variety of ways familiar to those skilled in the art. The support may include, but is not limited to, polystyrenes, polyacrylamides, latex, silica, agarose, ferrous compounds, nylon, cellulose acetate, nitrocellulose, and the like. These supports may take the form of tubes, microwell plates, slides, beads, filters, etc.

The labeled antibody composition may be a polyclonal antiserum obtained from animals (e.g., rabbits, goats, or mice) immunized with HIV or fragments thereof by methods known to those skilled in the art. Antisera may also be obtained from humans previously exposed to HIV and containing high titers of antibodies to the virus.

Biological fluids or samples may also be directly examined for the presence of HIV antigens by first affixing the specimen to a solid support, which may be accomplished in a variety of ways. Polystyrene can be used as a solid support (e.g., as microwell plates) or, alternatively, the sample may be attached to other solid supports including nylon, cellulose acetate, nitrocellulose or other membranes as well as glass, polyacrylamide, etc. The affixed samples are incubated with the desired monoclonal antibody or with a composition comprised of two or more monoclonal antibodies specific for HIV epitopes contained within different antigenic regions under conditions conducive to immune complex formation. The antigen-antibody complex is then washed and signal detected when a primary antibody is used. If the first antibody is unlabeled, a second labeled immunoglobulin-specific antibody is added. Thereafter, the presence of the label specifically bound to the antigen-antibody complex is determined.

Kits can also be supplied for use with the subject monoclonal antibodies of the present invention in the detection of HIV infection or for the presence of HIV antigen. Thus, the subject monoclonal antibody composition of the present invention may be provided, usually adsorbed to a solid phase or in a lyophilized form, either alone or in conjunction with additional antibodies specific for other antigenic determinants of HIV. The antibodies, which may be conjugated to a label or unconjugated, are included in the kits with buffers, such as Tris, phosphate, carbonate, etc., stabilizers, biocides, inert proteins, e.g., bovine serum albumin, or the like. Generally, these materials will be present in less than about 5% wt. based on the amount of active antibody, and usually present in total amount of at least about 0.001% wt. based again on the antibody concentration. Frequently, it will be desirable to include an inert extender, or excipient to dilute the active ingredients, where the excipient may be present in from about 1 to 99% wt. of the total composition. Where a second antibody capable of binding to the monoclonal antibody is employed, this will usually be present in a separate vial. The second antibody is typically conjugated to a label and formulated in an analogous manner with the antibody formulations described above. The kits themselves comprise compartments containing vials or other containers for the reagents described above which are necessary for the performance of the particular diagnostic immunoassay. Such kits may find considerable utility in monitoring the presence or replication of the virus in vitro, particularly in studies where the efficacy of anti-HIV drugs is assessed. The treatment of humans or animal model systems with possible therapeutic drugs or vaccines may be monitored via the methods of the instant invention.

Other features and advantages of the present invention will become apparent from the following experimental descriptions, which describe the invention by way of example. The examples are offered by way of illustration and not by way of limitation.

EXAMPLE I

Example I demonstrates methods for the production of hybrid cell lines which produce monoclonal antibodies that react with proteins and antigenic fragments of HIV containing the desired antigenic determinants. These monoclonal antibodies were characterized by their ability to react with HIV antigens in ELISAs, immunoblots, radioimmunoprecipitation and indirect immunofluorescence assays. The antigenic determinants with which the antibodies reacted were identified in ELISA assays using bacterial expressed fusion proteins and synthetic peptides which comprise regions of antigenic determinants of HIV core proteins.

Hybrid cell lines were produced by fusing myeloma cells with lymphoblastoid cells obtained from animals immunized with HIV antigens. Initially, purified virus disrupted in detergent was used to immunize host animals, and this resulted in antibodies specific for core (gag) proteins and precursors. The LAV-1 strain of HIV was purified from infected CEM cells (ATCC #CRL 8904) on a 30-40% discontinuous sucrose gradient and pelleted. The purified virus was disrupted in 0.5% Triton X-100 (Triton is a registered trademark of the Rohm & Haas Co. for octylphenoxypolyethoxyethanol) and fixed with 1% formalin. This suspension was mixed in a 1:1 ratio with Freunds incomplete adjuvant, and 100 ul used to immunize the mice. Boosters were given at weeks two and three, and sera were monitored for the production of antibodies by the immunized mice. When anti-HIV circulating antibodies were detected by ELISA, immunoblot and RIP, the animals' spleens were removed and the splenocytes used in cell fusions as described below.

A bacterially-expressed fusion protein from the gag region of HIV was also used as an immunogen. The pGAG3 construct, from about base pair (bp) 691 through bp 1642 (numbering according to Wain-Hobson et al., 1985, Cell 40:9), was inserted into the B-galactosidase gene and expressed in E. coli. The expressed protein was purified from the expression system and used as an immunogen in compositions with Freunds complete adjuvant. Booster injections were given about two weeks apart. One week following the second boost the mice were bled and tested for circulating antibody to the disrupted virus and other desired molecules by ELISA, radioimmunoprecipitation (RIP) and immunoblot. Splenocytes from animals with the appropriate immune response were used in cell fusions.

Protocols used for the generation of cell lines were generally those of Kohler and Milstein (*Nature* 256:495 (1975)) with modifications (Goldstein, et al., 1982, *Infect. Immun.* 38:273). Splenic B-lymphocytes from the immunized mice were fused with NS-1 myeloma cells using 40% (w/v) polyethylene glycol. Following fusion the cell mixture was resuspended in HAT medium (RPMI-1640 medium supplemented with 15% fetal calf serum, $1 \times 10^{-4}$ M hypoxanthine, $4 \times 10^{-7}$ M aminopterin and $1.6 \times 10^{-5}$ M thymidine) to select for the growth of hydrid cells, and then dispensed into 96-well microculture trays at a concentration of 1 to $3 \times 10^6$ cells/ml with an approximately equal number of mouse thymocytes and incubated at 37° C. in a humidified atmosphere containing 6% $CO_2$. Cultures were fed by replacing one-half of the culture medium with fresh HAT medium and wells were observed for cell proliferation with an inverted microscope. When cells in a well were of a sufficient density the medium was tested for anti-HIV antibody and reactivity with various HIV antigens.

Wells containing hybrid cells producing antibody to HIV or recombinant HIV proteins were identified by ELISAs measuring the binding to either purified whole disrupted virus or biologically-expressed gag or env fusion proteins (see copending and commonly owned U.S. patent applications Ser. Nos. 763,460, 828,828, and 721,237). ELISA assays using disrupted virus were carried out on LAV EIA plates (Genetic Systems, Seattle, Wash.). ELISA plates using recombinant fusion proteins were prepared by dissolving the recombinant protein in 0.05M carbonate/bicarbonate buffer to a final concentration of about 2 ug/ml. The suspension was aliquoted into plate wells and incubated at 4° C. overnight. The plates were then blocked with blocking reagent, 5% non-fat dry milk, 0.01% thimerosol, 0.01% antifoam A, in PBS. Plates were incubated with spent cell culture medium at 37° C. for 45 minutes and then washed three times with 0.05% Tween 20 in PBS (PBS-Tween). Peroxidase-goat anti-mouse IgG (1:2,000 dilution in PBS-Tween; Zymed Laboratories, Inc., South San Francisco, Calif.) was added (100 ul per well), and the plates were incubated for 45 minutes at 37° C. and washed as above. Substrate (0.025M citric acid, 0.05M dibasic sodium phosphate, pH 5.0 containing 14 mg of o-phenylenediamine and 10 ul of 30% hydrogen peroxide per 50 ml) was added and the plates were incubated for 30 minutes at room temperature in the dark. The reaction was stopped with 3N sulfuric acid and colorimetric reactions were quantitated with an automated microplate reader. Wells that gave positive results were subcloned by limiting dilution, retested for specificity, then expanded.

Cell lines were further characterized as to specificity and reactivity by immunoblotting, immunoprecipitation and ELISA using disrupted HIV virus, recombinant HIV fusion proteins and synthetic HIV peptides. Designations of regions encompassed by the recombinant fusion protein and synthetic peptides are described in Tables I and II.

TABLE I

| Recombinant Fusion Proteins From the GAG Region | | |
|---|---|---|
| Name | Base Pair Number* | ATCC Accession Number |
| GAG1 | 375-961 | 53379 |
| GAG2 | 631-1224 | 53111 |
| GAG3 | 691-1642 | 33112 |

*Numbering according to Wain-Hobson et al., 1985, Cell 44:9. The production of the recombinant fusion proteins is described in detail in commonly owned U.S. Pat. applications, Ser. Nos. 763,460 and 828,828, which are incorporated herein by reference.

TABLE II

| Synthetic Peptides From the GAG Region | | |
|---|---|---|
| Name | Residue Number | Base Pair Number |
| 15 | 329-350 | 1320-1385 |
| 88 | 315-350 | 1278-1385 |
| 141 | 198-242 | 927-1061 |
| 147 | 278-319 | 1167-1292 |

The various methods used to further characterize the specificity of the monoclonal antibodies of the present invention are described below. A summation of the results is found in Table III.

Characterization by immunoblotting was carried out on clone supernatants or ascites fluid using purified, detergent disrupted LAV virus and recombinant fusion proteins as antigens. The recombinant proteins were from the gag region and included Gag-1 (bp375-961), Gag-2 (bp631-1224) and Gag-3 (bp691-1642). The antigens were first separated by polyacrylamide gradient gel electrophoresis (7.0-15.0%) and transferred to nitrocellulose membrane (NCM) by electrophoresis for four hours at 25 V in 25 mM sodium phosphate (pH 7.0). After transfer, the NCM was blocked to prevent non-specific interactions by incubation in blocking reagent (5% non-fat dry milk, 0.01% thimerosol, 0.01% antifoam A, in PBS) for one hour at room temperature. The NCM was incubated with cell culture supernatant or ascites fluid diluted in PBS-Tween for one hour at room temperature and was rinsed with three changes of PBS-Tween. In the second step the NCM was incubated with goat anti-mouse IgG-horseradish peroxidase diluted in PBS-Tween for one hour at room temperature. This incubation was followed by washing with PBS-Tween and then immersion in horseradish peroxidase color development solution (Bio-Rad Laboratories, Richmond, Calif.) for 20 minutes. The reaction was stopped by immersion in deionized water. Monoclonal antibody reactivity was compared to a positive control serum reactive with purified disrupted virus or expressed fusion protein.

Viral extracts for radioimmunoprecipitation were prepared from CEM cells infected with the LAV-1 isolate of HIV adapted to lytic growth by continuous passage. When early cytopathic effects were evident, the cells were transferred to labeling media containing $^{35}$[S]-methionine (0.05 mCi/ml) or $^{3}$[H]-glucosamine (0.025 mCi/ml), then incubated for 24 h until most of the cells had lysed, releasing virus into the culture supernatant. Virus was pelleted (one hour at 100,000 xg) from the cell-free supernatant, and detergent extracts were prepared in P-RIPA buffer (phosphate buffered saline containing 1.0% Triton X-100, 1.0% deoxycholate, 0.1% SDS, and 1% Aprotinin). Similar extracts were prepared from uninfected CEM cells.

Immunoprecipitation assays were performed with 100 ul of virus extract incubated with 100 ul culture supernatant from the hybrid cell lines for one hour on ice. Four microliters of rabbit anti-mouse Ig (Zymed Laboratories, So. San Francisco, Calif.) was added to each sample and incubated for 30 minutes. Immunoprecipitin (100 ul; Bethesda Research Laboratory, Bethesda, Md.) resuspended in P-RIPA buffer containing 1.0% ovalbumin was added to each sample and incubated for an additional 30 minutes. The bound complexes were washed and separated by SDS-polyacrylamide gel electrophoresis (15.0% acrylamide:DATD gel). Following electrophoresis the gels were fixed, soaked in EnHance (New England Nuclear, Boston, Mass.), dried and exposed to Kodak XR-5 film. A positive reference serum which immunoprecipitated all HIV viral proteins was reacted with viral-infected and mock-infected CEM cell supernatants as positive and negative controls.

The results, summarized in Table III, showed that four monoclonal antibodies specifically immunoprecipitated p25 and the gag precursor proteins p55 and p40. Each of the monoclonal antibodies was of the IgG1 isotype.

Characterization by indirect immunofluorescence was carried out by gently pelleting infected CEM cells (approx. $1 \times 10^6$ cells/ml) at low speed and washing the cells twice with cold PBS and resuspending in the same volume. Twenty microliters of the cell suspension was dropped into each well of Multiwell slides (Carlson) and allowed to air dry for two hours. Cells were fixed to the slides by immersion in 100% acetone or methanol-acetone (1:1) for 10 minutes at room temperature. Slides were allowed to dry and were stained immediately thereafter or stored at $-20°$ C. with dessicant.

Antibody ascites was diluted 1:100 in PBS and 20 ul was dropped into each well. Slides were incubated for 45 minutes at 37° C. in a humidified chamber before aspiration of the antibody solution and washing twice with PBS. The excess PBS was aspirated from the area around each well without allowing the cells to dry. FITC-goat anti-mouse F(ab') (Zymed Laboratories) was diluted 1:50 or 1:100 and 20 ul was added to each well. This was incubated with the cells for 30 minutes at 37° C. in a humidified chamber. Slides were again washed with PBS followed by a distilled water wash. The cells were counter stained with Evan's Blue (0.05% in PBS) for one minute with a distilled water wash.

Slides were examined with a fluorescent microscope for positive reactions.

Alternatively, the infected cells could be incubated directly with the monoclonal antibodies (for 45 minutes at 37° C.) before being dropped onto the Multiwell slides and allowed to air dry. The slides could then be fixed with acetone or methanol:acetone as above. The remaining steps in the procedure would be the same as those described above. All of the monoclonal antibodies react with HIV infected cells by the immunofluorescent assay.

To map the regions containing the antigenic determinants which were recognized by the monoclonal antibodies of the present invention, culture supernatants from hybrid cell lines or ascites fluid were further characterized by their reactivity in ELISAs with synthetic peptides. The ELISA procedure was the same as that described above except that synthetic peptides replaced disrupted virus or fusion protein as the antigen adsorbed to the surface of the microwells. When peptides were used as the antigen the plating protocol was as follows. Lyophilized peptide was dissolved in 6M guanidine HCl; just prior to plating in the 96 well plates, the guanidine solution was diluted into 0.05M carbonate/bicarbonate buffer (pH 9.6) to a final peptide concentration of up to 100 ug/ml. A 50 ul volume of the dilute peptide solution was added to each well of the microtiter plate and the plates were then incubated overnight at 4° C. Excess peptide solution was "shaken out," plates were blocked with blocking reagent, and the procedure described above for the ELISA of disrupted virus was followed. The results are summarized in Table III. Monoclonal antibodies produced by cell lines specific for core proteins reacted with recombinant fusion proteins from the gag region. Monoclonal antibodies from the cell lines HIV p25-2 and HIV p25-3 reacted with all three gag fusion proteins tested. Monoclonal antibodies from cell lines HIV p25-6 and HIV p25-7 reacted only with GAG3. The antigenic determinants containing the epitopes with which the monoclonal antibody reacted were narrowed to smaller regions by their reactivity with synthetic peptides, except for antibody 25-2. The peptides with which each of the monoclonal antibodies react are found in Table III.

To further exemplify the utility of this invention the monoclonal antibodies were used in the following examples to detect the presence of HIV in a variety of specimens and assay formats.

TABLE III

| | Characterization of Mouse Monoclonal Antibodies | | | | | | | |
|---|---|---|---|---|---|---|---|---|
| Antibody | LAV Proteins | Recombinant Proteins | Peptides | Assay Methods | | | | Immunogen* |
| | | | | Blot | RIP | EIA | FA | |
| 25-2 | p25/ p40/ p55 | GAG-1, -2, -3 | ND[1] | + | + | + | + | B |
| 25-3 | p25/ p40/ p55 | GAG-1, -2, -3 | 141 | + | + | +/− | + | B |
| 25-6 | p25/ p40/ p55 | GAG3 | 147 | + | + | + | + | A |
| 25-7 | p25/ p40/ p55 | GAG3 | 15, 88 | + | + | + | + | B |

*Immunogen: A. Whole inactivated virus, B. Recombinant gag fusion protein.
[1]ND - Not Determined

EXAMPLE II

Single Wash HIV Antigen Capture Enzyme-linked Immunosorbent Assay

Example II describes a single wash format of an antigen capture enzyme-linked immunosorbent assay (EIA) where monoclonal antibodies derived from hybrid cell lines HIV p25-2 and HIV p25-3 were used to capture antigen and purified immunoglobulin from a high titered human sera conjugated to horseradish peroxidase was used to detect captured antigen. A 2 hour and overnight (16–18 hours) incubation format with an antigen containing sample are described.

a. Conjugation of Purified Immunoglobulin and Horseradish peroxidase

Immunoglobulin from high titered AIDS positive human sera was purified by precipitation in 40% ammonium sulfate, extensive dialysis and elution from a DE-52 cellulose column (Whatman). Purified immunoglobulin was conjugated to horseradish peroxidase (Calbiochem) using the procedure of Nakane et al. (*J. Histochem. Cytochem.*, 1974, 22: 1084) with the following modifications. Purified immunoglobulin was adjusted to 4.0 mg/ml and dialyzed against 0.2M sodium carbonate/1M NaCl pH 9.5. Purified Horseradish Peroxidase (HRP) was oxidized with 0.07M sodium periodate and conjugated to the immunoglobulin using a molar ratio of 1:5 (ab:HRP) for 30 minutes. The reaction mixture was stopped with sodium borohydride. The resultant product was precipitated with 50% saturated ammonium sulfate and the precipitate dialyzed against a buffer of 100 mM TRIS/1M NaCl. The conjugate was then adjusted to 4 mg/ml and diluted to 2 mg/ml with glycerol.

b. Standard Curve with Purified Virus in Human Plasma and Cell Culture Media Ascites derived from hybridoma cell lines HIV-p25-2 (ATCC No. HB9407) and HIV-p25-3 (ATCC No. HB9408) were diluted 1:5,000 in 25 mM Tris buffer, pH 8.5, and 200 ul was added to each well of Nunc microtiter strips. The strips were sealed and incubated for about 16–18 hours at room temperature. Antibody solution was removed from the well by aspiration before a blocking solution of 0.3% BSA, 5% sucrose in PBS was added and incubated for 60 minutes at room temperature. Blocking solution was removed by aspiration and the strips were allowed to air dry at room temperature. The strips could then be used immediately or could be stored for up to eight months at 4° without significant loss of reactivity.

Samples were made up of 0–500 pg/ml purified inactivated virus (LAV) diluted in either normal human plasma or cell culture media. Two hundred microliters of each virus concentration was added to each of three wells with 50 ul of Triton X-100 in water. For the test employing a 2 hour incubation period, 50 ul of immunoglobulin/HRP conjugate (about 100 ug/ml) in 1% normal goat serum, citrate buffer, pH 7.0 was added and the wells incubated 2 hours at 37° C. with gentle agitation. In the overnight (16–18) format, the samples in Triton X-100/water were incubated in the wells overnight at 37° C., and then the conjugate added, followed by an additional 2 hour incubation at 37° C. The solution was then removed from the wells by aspiration and the wells were then washed with 0.05% Tween 20 in 0.15M NaCl six times. Two hundred microliters of substrate (80 ug/ml tetramethylbenzidine, 0.0015% hydrogen peroxide, citrate/phosphate buffer, pH 6.0) was added to each well and incubated at room temperature for 30 minutes before the reaction was stopped by the addition of 1N $H_2SO_4$ and colormetric reactions were quantitated by the optical density ratio at 450:630 nm.

Results for the 2 hour and 24 hour formats of the single-wash HIV antigen EIA in normal human sera and cell culture media are shown in Table IV. The sensitivities of each format were extrapolated from the results and about 59 pg/ml of virus can be detected in normal human plasma and about 70 pg/ml of virus in cell culture media using the 2 hour format while 32 pg/ml of virus is detectable in both normal human plasma and cell culture media using the longer, 16–18 hour, incubation step.

TABLE IV

Standard Curves of Virus Detection in Normal Human Plasma and Cell Culture Media

| HIV Antigen (pg/ml) | Plasma | | Cell Culture Media | |
|---|---|---|---|---|
| | 2 Hour Incubation (S.D.)[1] | 24 Hour Incubation (S.D.) | 2 Hour Incubation (S.D.) | 24 Hour Incubation (S.D.) |
| 500.0 | 0.419(.008) | 1.235(.020) | 0.527(.002) | 1.400(.013) |
| 250.0 | 0.245(.008) | 0.682(.007) | 0.281(.013) | 0.690(.014) |
| 125.0 | 0.125(.013) | 0.405(.008) | 0.181(.001) | 0.380(.009) |
| 62.5 | 0.082(.004) | 0.200(.003) | 0.122(.005) | 0.215(.001) |
| 31.0 | 0.058(.003) | 0.127(.006) | 0.100(.003) | 0.139(.014) |
| 15.5 | 0.047(.008) | 0.072(.002) | 0.097(.011) | 0.081(.001) |
| 8.0 | 0.039(.002) | 0.049(.001) | 0.093(.004) | 0.060(.002) |
| Neg. Cntrl. | 0.028(.002) | 0.031(.005) | 0.088(.001) | 0.039(.003) |

[1] S.D. - Standard Deviation c. Specificity of Single Wash Format HIV Antigen Capture EIA

The specificity of the HIV antigen capture EIA for detecting only antigen of HIV-1 isolates was demonstrated by testing HIV isolates including LAV-1, -4, -5, -6, LAI, ELI (Pasteur Institute, Montagnier), ARV-2 (Levy, et al.), CF-65 and CF-70 (Genetic Systems Corp., Seattle, Wash.) and heterologous virus including Human T cell Leukemia Virus I (HTLV-1), Simian T Cell Lymphotropic Virus III (STLV-III), Epstein-Barr Virus (EBV), and Cytomegalovirus (CMV) as well as the HUT and CEM transformed human cell lines. Viruses were grown using methods outlined above. After periods of about 3–7 days cell culture supernatants were removed and 200 ul was added to microtiter wells and assayed by the HIV antigen capture EIA described in Example IIb. All HIV-1 isolates were positive in the HIV antigen capture EIA and none of the heterologous viruses was cross reactive.

d. HIV Antigen Capture EIA of Normal Donor Serum and Plasma Samples

The HIV antigen capture EIA for detection of antigens in serum or plasma specimens from a normal donor population was tested. A total of 500 serum or plasma specimens were tested in the overnight format of the HIV antigen detection EIA described in Example IIb. A summary of the results for the donor population screen indicates that 488 (97.6%) of the population were non-reactive and 12 (2.4%) were initially reactive. Of the twelve that were initially reactive, none was repeatably reactive.

e. Two Wash Format of the HIV Antigen Capture EIA Using Monoclonal Antibody for Capture and Detection of Antigen Example IIe illustrates an alternate format for the HIV antigen capture EIA which uses a wash step between the addition of the capture and detection antibodies. Also in this example monoclonal antibodies derived from the hybrid cell lines HIV-p25-6 (ATCC No. HB9409) and HIV-p25-7 (ATCC No. HB9410) were conjugated to horseradish peroxidase and were used in the detection step. A clinical feasibility panel of sera from different diagnostic groups was tested by this assay format.

The wells of the microtiter strips were coated with monoclonal antibodies 25-2 and 25-3, sample preparation, and incubation were as described in Example IIe. Serum and plasma samples were selected from the AIDS, ARC, LAS, healthy homosexual and normal donor populations. Following the incubation of the sample with the adsorbed monoclonal antibodies the sample was aspirated from the wells and the wells were washed with 0.05% Tween 20 in 0.15M NaCl.

Monoclonal antibodies 25-6 and 25-7 from ascites fluid purified were conjugated with horseradish peroxidase as described in Example IIa and diluted 1:3,000 in a diluent containing 20% immunoglobulin free mouse ascites fluid, 5% unrelated isotypic monoclonal antibody, 5% bovine serum albumin, 0.01% thimerosal, and 0.005% gentamicin in 150 mM NaCl, 50 mM Tris, pH 7.2. Dilute conjugate, 200 ul, was added to each well and incubated for 1 hour at 37° C. before washing the wells as above. The remainder of the assay was carried out as described for the one wash assay described above.

Results obtained with the two wash monoclonal antibody capture/monoclonal antibody detection HIV antigen capture EIA with a clinical feasibility panel are given in Table V. Within the various diagnostic groups 75% of AIDS patients were positive for antigen, 57% of ARC, 17% of LAS, 12% of healthy homosexuals and none of the normal human sera samples was found to be positive for antigen.

TABLE V

Clinical Feasibility Panel, Two Wash Monoclonal/Monoclonal HIV Antigen Capture EIA Format

| Diagnostic Group | | | | | |
|---|---|---|---|---|---|
| AIDS | ARC | LAS | Healthy Homosexual | Normal Human Sera | Negative Control |
| 0.118[1] | 0.076 | 0.058 | 0.088 | 0.057 | 0.059 |
| 0.154 | 0.080 | 0.064 | 0.090 | 0.058 | 0.068 |
| 0.207 | 0.083 | 0.068 | 0.096 | 0.082 | 0.072 |
| 0.210 | 0.139 | 0.075 | 0.100 | 0.084 | 0.073 |
| | 0.161 | 0.076 | 0.104 | 0.085 | 0.074 |
| | 0.198 | 0.079 | 0.107 | 0.086 | 0.078 |
| | 0.213 | 0.083 | 0.110 | 0.089 | 0.084 |
| | | 0.085 | 0.143 | 0.093 | |
| | | 0.088 | | | |
| | | 0.091 | | | |
| | | 0.092 | | | |
| | | 0.095 | | | |
| | | 0.095 | | | |
| | | 0.097 | | | |
| | | 0.099 | | | |
| | | 0.101 | | | |
| | | 0.102 | | | |
| | | 0.116 | | | |
| | | 0.120 | | | |
| | | 0.123 | | | |
| | | 0.131 | | | |
| | | 0.471 | | | |
| | | 0.643 | | | |

[1] Optical density values below the line are greater than the cutoff value which was determined by taking the mean of the negative control and adding 0.050 optical density units. In this case the cutoff value was 0.123.

EXAMPLE III

Seroconversion of Chimpanzees Tested by HIV Antigen Detection and Antibody Detection Methods are needed to monitor the effectiveness of various vaccine and therapeutic preparations as they are tested in animals and humans. In Example III the HIV antigen detection method of the instant invention is compared to a commercially available HIV antibody screening kit.

A chimpanzee was pre-bled and inoculated with HIV. Every two weeks the animal was bled and monitored for both antigen and antibody levels with the one wash overnight HIV antigen detection method described in Example IIb and the Genetic Systems LAV EIA Kit (Genetic Systems Corporation, Seattle, Wash.). Results are seen in Table VII and are summarized as follows. Antigen could be detected during the second week and before antibody levels were detectable. Antibody titers were detectable the fourth week after inoculation and increased through week twelve. Antigen levels decreased from week four as the antibody level increased. The data suggest that there is a period of time when an animal is potentially infectious before antibodies are detectable. The antigenemia detected using the monoclonal antibodies of the present invention may be an earlier indicator of HIV infection in animals than antibody seroconversion.

TABLE VII

Comparison of HIV Antigen Detection and Antibody EIA in Testing for Seroconversion in a Chimpanzee

| Serum Sample | Antigen Detection | Antibody Detection |
|---|---|---|
| pre-bleed | 0.118 | 0.085 |
| week 2 | 0.497 | 0.086 |
| week 4 | 0.209 | 0.284 |
| week 6 | 0.032 | 0.818 |
| week 8 | 0.038 | 1.464 |
| week 10 | 0.036 | 1.947 |
| week 12 | NT[1] | 2.045 |

[1] NT = Not Tested

On or about Apr. 30, 1987, the hybridomas HIV-p25-2, HIV-p25-3, HIV-p25-6, and HIV-p25-7 were deposited with the American Type Culture Collection, 12301 Parklawn Drive, Rockville, Md. and assigned accession numbers ATCC HB 9407, HB 9408, HB 9409 and HB 9410, respectively.

What is claimed is:

1. A method for detecting and/or quantitating HIV in a biological sample suspected of containing HIV or antigenic determinants of HIV, said method comprising:
   a) incubating the sample with capture monoclonal antibodies obtained from HB 9407 and/or HB 9408, and, either simultaneously or sequentially, with a labelled antibody composition binding to antigenic determinants of HIV, such that specific binding occurs, thereby forming a reaction mixture; and
   b) detecting the reaction mixture formed in step (a) to determine the amount of label associated with the antigenic determinants and thereby detecting and/or quantitating HIV or antigenic determinants of HIV present in the sample.

2. The method of claim 1, wherein the labeled antibody composition is one or more monoclonal antibodies.

3. The method of claim 2, wherein the monoclonal antibody is obtained from cell line HB 9408 or HB 9409.

4. The method of claim 1, wherein the labeled antibody composition is a polyclonal antiserum.

5. The method of claim 4, wherein the polyclonal antibodies are obtained from a human previously exposed to HIV and containing antibodies to said virus.

6. The method of claim 1, wherein the capture monoclonal antibodies are immobilized on a solid phase.

7. The method of claim 1, wherein the label is selected from the group consisting of radionuclides, fluorescers, enzymes, enzyme substrates, enzyme cofactors, enzyme inhibitors, and ligands.

8. The method of claim 1, wherein the sample is selected from the group consisting of bodily secretions, bodily fluids, tissue specimens, cultured cells, and cell culture supernatants.

9. The method of claim 1, wherein the step of detection is by enzyme reaction, fluorescence, radioactivity, cell lysis, or luminescent emission.

10. A kit for use in detecting the presence of HIV antigens, said kit comprising compartments containing in a first compartment a monoclonal antibody obtained from cell line ATCC No. HB 9407 or HB 9408 and a second compartment containing a second monoclonal antibody obtained from ATCC No. HB 9409 and labels providing for a detectable signal covalently bonded to said second monoclonal antibody or bonded to antibodies specifically reactive with said second monoclonal antibody.

11. The cell line ATCC No. HB 9407, HB 9408 or HB 9409.

12. A monoclonal antibody produced by a cell line of claim 11.

* * * * *